United States Patent [19]
Kesten et al.

[11] 4,346,752
[45] Aug. 31, 1982

[54] SELF-DRIVEN CHEMICAL HEAT PIPE

[75] Inventors: Arthur S. Kesten, West Hartford;
Alan F. Haught, Glastonbury, both of Conn.

[73] Assignee: United Technologies Corporation, Hartford, Conn.

[21] Appl. No.: 226,320

[22] Filed: Jan. 19, 1981

[51] Int. Cl.³ .............................................. F28D 21/00
[52] U.S. Cl. .................................. 165/1; 165/104.12; 165/104.21; 165/104.25
[58] Field of Search ......... 165/104.12, 104.21–104.27, 165/DIG. 17

[56] References Cited
U.S. PATENT DOCUMENTS 308,197 11/1884 Rober ............................. 165/104.12
4,192,371 3/1980 Derouette et al. .............. 165/104.12
4,216,903 8/1980 Giuffre ............................. 165/104.21

OTHER PUBLICATIONS

R. L. McKisson, *Dissociation—Cooling: A Discussion* Livermore Research Laboratory of the A.E.C., Livermore, Calif., 3/54, pp. 1-20, LRL—86.

N. G. Aabalu et al., *Chemical Heat Pipe*, IBM Technical Disclosure Bulletin, vol. 13, No. 12, p. 3812, 5/71.

Primary Examiner—Albert W. Davis
Attorney, Agent, or Firm—Stephen A. Schneeberger

[57] ABSTRACT

A method and apparatus for a self-driven chemical heat pipe are provided in a circuit including an endothermic reaction chamber and an exothermic chamber connected by a pair of arms extending therebetween. Reactant is endothermically reacted near the heat source to create reaction product at a pressure greater than exists at the exothermic reaction chamber to promote flow thereof through one of the arms. Reaction product is exothermically reacted in the exothermic reaction chamber near the heat sink to liberate heat and form recombined gaseous reactant. That gaseous reactant is converted to liquid form, which liquid-form reactant occludes part of the other arm and flows therethrough toward the endothermic chamber to complete the cycle. The liquid occlusion of that arm ensures adequate unidirectional flow about the circuit. Provision may be made for selectively reversibly storing reaction product or reactant to accommodate differences in time between heat production at the source and heat demand at the sink.

29 Claims, 10 Drawing Figures

SELF-DRIVEN CHEMICAL HEAT PIPE

TECHNICAL FIELD

The present invention relates to the method of and apparatus for transporting thermal energy and more particularly to the transport of heat as chemical energy. More specifically, the present invention relates to a self-driven system for the transport of heat in the form of chemical energy.

BACKGROUND ART

Various techniques have been employed for transferring or transporting thermal energy between a thermal source and a thermal sink or load. In some instances, there is relatively little concern for the amount of heat which may be lost, as by radiation, convection or conduction during the transport process, either because the transport distance is small and the loss is slight or because of an excessive amount of thermal energy available for transport. In other instances however, it is desired to transfer the heat as efficiently as possible and heat pipes have been especially useful in accomplishing that end. A heat pipe is generally considered a closed-loop two cycle system. In a vaporization/condensation type of heat pipe, there is a rapid heat transfer into the pipe resulting in evaporation of a working fluid therein. The evaporated working fluid builds up sufficient pressure to be transmitted along the pipe and is then condensed at the other end thereof. The cycle is completed by returning the condensate to the evaporating end by means of capillary or other action through a wick or other suitable means within the pipe. Typically, the working fluid may be water, freon, methyl alcohol, acetone or the like. However, because the working fluid is at an elevated-temperature vaporized state while transporting thermal energy from the heat source to the heat sink, it may experience significant radiation, convection and conduction losses to the environment which is normally at a significantly lower temperature. These losses may be considerable if the transport path length is particularly long and therefore such vaporization/condensation heat pipes are generally used only where the distance over which the heat is to be transported is relatively short or insignificant, as for instance less than ten feet.

In many instances, however, it is desired or required to transport thermal energy over relatively long or significant distances from tens or hundreds of feet to as much as tens or hundreds of miles. To accomplish such transport in a relatively efficient manner, resort has been made to chemical heat pipe systems in which a reactant or reactants within the system undergo a first chemical reaction at the heat source and a second chemical reaction at the heat sink. That first chemical reaction is of an endothermic nature in which heat is chemically absorbed by the reaction process and the second reaction is an exothermic reaction during which heat is chemically liberated during the reaction process. Importantly, the reactant and/or reaction products may exist and be transported at temperatures which do not differ substantially from that of the environment, thereby greatly reducing the potential for thermal loss from the system. These chemical reactions are generally reversible and are generally effected and/or accelerated by a catalyst at one or both of the reaction sites.

Examples of such chemical heat pipes, especially for the delivery of thermal energy over long distances as from a nuclear reactor to remote industrial and/or residential heat sinks, are disclosed in the following U.S. Pat. Nos. 3,198,710 issued Aug. 3, 1965 to R. B. Long; 3,558,047 issued Jan. 26, 1971 to Wolfgang et al; 3,690,550 Sept. 12, 1972 to Hilberath et al; 3,967,676 issued July 6, 1976 to H. S. Spacil; 4,044,821 issued Aug. 30, 1977 to J. C. Fletcher; 4,091,864 issued May 30, 1978 to Cocuzza et al; and 4,169,499 issued Oct. 2, 1979 to LeFrois. The U.S. Pat. Nos. 4,044,821 and 4,169,499 are examples of systems in which thermal energy from a source at one temperature is transported for use at a substantially higher temperature at the thermal sink. The remainder of the above cited U.S. patents generally transfer thermal energy from a high temperature heat source to a relatively lower temperature heat sink. A variety of reactants have been used in those systems including cyclohexane and/or possibly methylcyclohexane in U.S. Pat. Nos. 3,198,710 and 4,044,821, phosgene in U.S. Pat. No. 3,967,676, urea in U.S. Pat. No. 4,169,499, sulphur trioxide in U.S. Pat. No. 4,091,864 and ethane and/or methane in U.S. Pat. Nos. 3,558,047 and 3,690,550. The systems disclosed in the aforementioned patents normally provide various supplemental means for transporting the reactant or reactants and the products of reaction between the heat source and heat sink. Typically, one or more pumps and/or blowers are provided in the system's flow path for effecting the requisite reactant transport. These driving or transport mechanisms represent a cost in the system in terms of the equipment itself and/or the energy consumed to drive the pumps. This cost may be considerable if the system is of large capacity and/or is to transport the reactant for significant distances, and in some instances may be such as to negate the advantages otherwise afforded by such a system.

Accordingly, it is a principal object of the present invention to provide a method and apparatus which efficiently transports thermal energy for significant distances. Included in this object is the provision of an improved chemical heat pipe.

It is the further object of the present invention to provide a chemical heat pipe which effects transport of the working medium without inclusion of a conventional active driving mechanism. Included within this object is the provision of a self-driven chemical heat pipe which utilizes the properties of the reactant and reaction products and system geometry to effect a requisite flow of the working medium.

It is a still further object to provide a chemical heat pipe in accordance with the invention which is capable of selectively storing and releasing heat respectively to and from storage.

In accordance with the present invention, there is provided a method and apparatus for the efficient transport of thermal energy, particularly for relatively long distances in a self-driven system employing a chemical heat pipe. The heat pipe employs reversible endothermic and exothermic chemical reactions at respectively spaced heat source and heat sink positions therein for chemically transferring heat from a heat source to a heat sink. The chemical reactant or reactants provide the reversible endothermic/exothermic reactions, particularly in the presence of a suitable catalyst. A preferred type of reaction involves the dehydrogenation and hydrogenation of the reactant and the reaction products respectively, a preferred example of one such reactant being methylcyclohexane.

Importantly, the transport of the reactant and the reaction products which comprise the working medium of the heat pipe, is accomplished without requiring the insertion of conventional pumps into the heat pipe system. Instead, the chemistry of the reaction process and a selective valve technique within the heat pipe system operate to establish a substantially unidirectional flow of the reactant and reaction products within the closed circuit of the heat pipe system, which flow is operative to transfer relatively large quantities of thermal energy over significant distances. Moreover, operation of the heat pipe results in relatively little or no loss in the thermal energy transferred.

In a preferred embodiment, at least a portion of the flow conduit is occluded between the heat sink and the heat source positions with a liquid medium through which the reactant may flow but which effectively blocks the reverse flow of reaction products. The liquid medium is preferably caused to flow toward the heat source position, as by gravity, and fills a U-trap or the like, preferably near the heat source position. The liquid medium may preferably be the condensate of the reactant following its recombination from the reaction products at the heat sink. External cooling coils may effect the requisite condensation. Alternatively, the liquid medium may comprise a liquid solvent into which the recombined reactant is dissolved and through which that reactant is capable of passing to the heat source. The reactant in or from the liquid medium is delivered to the heat source position at which it undergoes vaporization and subsequent endothermic reaction in the presence of a catalyst.

In a further embodiment of the invention, the endothermic reaction product, normally in a gaseous form, is selectively diverted to a long-term storage device prior to arriving at the heat sink if no heat is required at the latter and is selectively retrievable from that storage for use at the heat sink when heat is needed thereat and is unavailable from the heat source. The reaction product constituent or constituents may be condensed and stored in liquid form and/or absorbed, as by adsorption, and stored. The process may be reversed to return the reaction products to the system for reaction at the heat sink.

BEST MODE FOR CARRYING OUT THE INVENTION

Figure 1:
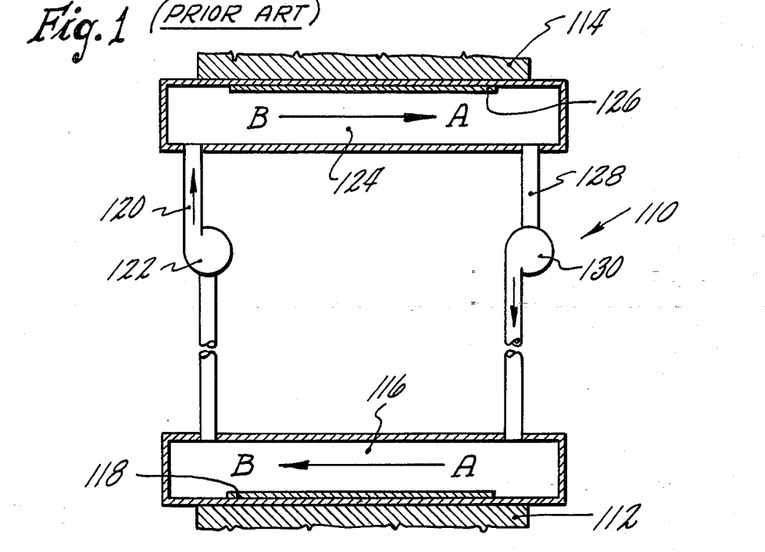
FIG. 1 is a diagrammatic representation of a prior art chemical heat pipe system.

Referring to the drawings, there is illustrated in FIG. 1 a chemical heat pipe system generally in accordance with the prior art. The system 110 is comprised of a closed loop, or closed circuit, flow path extending between a source of thermal energy, such as heat source 112, and a load for receiving thermal energy such as heat sink 114. Although the distance between heat source 112 and heat sink 114 may be as short as several feet, the advantages of a chemical heat pipe are most evident and best utilized when the distance is relatively long or significant, as for instance at least tens of feet and generally hundreds of feet to hundreds of miles. Reactant A within reaction chamber 116 adjacent heat source 112 is heated to a temperature by the heat source sufficient for it to undergo an endothermic chemical reaction in the presence of a catalyst 118. The product or products of that endothermic reaction have generally been designated B and will hereinafter be referred to as "reaction product". Typically, reactant A may be a hydrogen-containing compound and will undergo a dehydrogenation reaction and result in reaction product B. The thermal energy now stored chemically in reaction product B is transported via system arm 120, with the aid of one or more pumps or blowers 122, to a reaction chamber 124 adjacent the heat sink 114. The reaction product B undergoes an exothermic chemical reaction in the presence of a catalyst 126 in reaction chamber 124 to release thermal energy to the heat sink 114. This reaction recombines the reactant previously dissociated in reaction chamber 116, by hydrogenating the reaction product B and thereby reforming the reactant A. The recombined reactant A is then delivered via system arm 128 with the assistance of one or more pumps or blowers 130, to the heat source position within reaction chamber 116 to begin the thermal transfer cycle anew.

The prior art system 110 of FIG. 1 has been effective for transporting large quantities of chemically stored thermal energy for significant distances with relatively little loss; however, such systems have required the assistance of pumps or blowers 122, 130 to effect the requisite circulation or transport of the working medium within the system. These driving agents, i.e. pumps 122, 130, represent elements through which or by which energy is irretrievably lost and which represent an additional capital cost to the system as well as requiring periodic maintenance.

Figure 2:
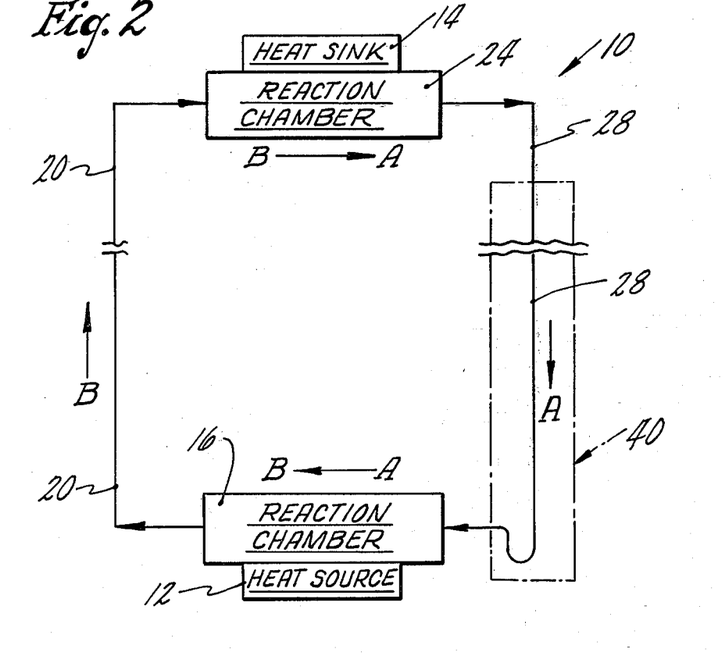
FIG. 2 is a generalized schematical diagram of the self-driven chemical heat pipe of the invention.

In accordance with the present invention, there is provided a self-driven chemical heat pipe system 10 as broadly illustrated in schematical form in FIG. 2. The reactant A undergoes endothermic reaction at a heat source position in reaction chamber 16 adjacent and in heat-transfer relationship with heat source 12 to form reaction product B, which product is transported via system arm 20 to a heat sink position in reaction chamber 24 adjacent to and in heat-transfer relationship with heat sink 14. In reaction chamber 24, the reaction product B undergoes exothermic reaction to release stored thermal energy to the heat sink 14. Both the dissociation of reactant A in chamber 16 and the recombination of reaction product B into reactant A in reaction chamber 24 are preferably conducted in the presence of respective catalysts. The reactant A is returned from reaction chamber 24 to reaction chamber 16 to resume the cycle anew; however, in accordance with the invention the system 10 does not require the pumps or blowers heretofore required for such long distance transport of the working medium.

Instead, the chemistry of the reaction process and the reactant pressure difference between the source and the sink, combined with a selective valve process within system 10 operate to establish a substantially unidirectional flow of the reactant and reaction products within the closed circuit of the heat pipe system, which flow is adequate for the transfer of large quantities of thermal energy over significant distances. In fact, a liquid-filled U-tube 40 appearing in return-arm 28 of system 10 between reaction chamber 24 and reaction chamber 16 effectively establishes a unidirectional flow of the medium within the system and thereby acts as a selective valve in a manner to be hereinafter more fully described.

Figure 3:
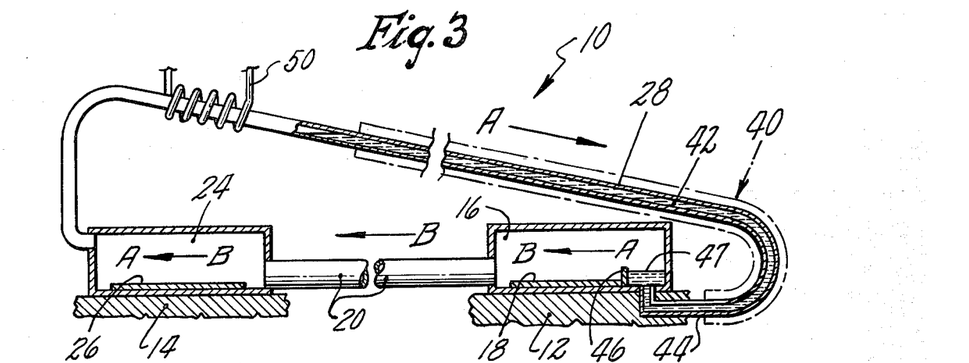
FIG. 3 is a diagrammatical illustration of a self-driven chemical heat pipe in accordance with one embodiment of the invention.

Referring to FIG. 3, there is illustrated a preferred embodiment of the self-driven chemical heat pipe 10 of the invention. The reactant A is selected to undergo endothermic reaction and become chemically dissociated into reaction product B within reaction chamber 16 in the presence of a suitable catalyst 18 at the heat source temperature. More specifically, reactant A may be a material which undergoes dehydrogenation in reaction action chamber 16, examples of such reactants being cyclohexane and methlcyclohexane which when dehydrogenated form the respective reaction products benzene and toluene, each accompanied by hydrogen. For the purpose of illustration herein, further discussion will be conducted in terms of methylcyclohexane as the reactant A herein, though it will be understood that many other suitable reactants might be substituted. Methylcyclohexane undergoes the following reaction by which it is dissociated into reaction product B, toluene and hydrogen, which are recombined by exothermic reaction at the heat sink to reform the methycyclohexane:

$$C_7H_{14} \rightleftarrows C_7H_8 + 3H_2$$

The methylcyclohexane reactant A, which may enter reaction chamber 16 in a liquid state as will be hereinafter described, is vaporized by the heat source 12 at high temperature, generally in excess of 600° F. at atmospheric pressure. The vaporized reactant then reacts endothermically, as promoted by a suitable catalyst 18, as for instance one from the platinum family, in the presence of the heat from heat source 12. This reaction dissociates or dehydrogenates the methylcyclohexane into reaction product B comprised of toluene and hydrogen in the gaseous state. Reaction product B is transported via arm 20 to reaction chamber 24 in a manner to be hereinafter more fully described. Reaction product B undergoes an exothermic reaction in reaction chamber 24, which reaction is promoted by catalyst 26 therein which may be nickel or the like. This exothermic reaction occurs at a temperature of about 300° F. at atmospheric pressure and results in the recombination or hydrogenation of the reaction product to reform the methylcyclohexane reactant A. The exothermic reaction releases chemically stored thermal energy to the heat sink 14.

The methylcyclohexane so reformed in reaction chamber 24 issues from an exit thereof into arm 28. Within arm 28 between reaction chamber 24 and reaction chamber 16 is provided the means for effecting a substantially unidirectional flow of the reactant A in such quantity as to afford the requisite transfer of thermal energy without the assistance of conventional driving or pumping means. The methylcyclohexane in its gaseous state is rapidly cooled upon exiting from reaction chamber 24 and entering arm 28, as by means of a condensing coil 50 positioned in effective heat transfer relation with the reactant A passing through arm 28. Condenser 50 may conveniently be positioned externally of heat pipe arm 28 in encircling relationship therewith. The rapid cooling of the gaseous reactant A converts it to its liquid state and effects a rapid decrease in its partial pressure. This condensed reactant A is readily conducted by gravity toward the reaction chamber 16 and accumulates as condensate 42 which fills and thereby occludes arm 28 over a portion of its length. In the embodiment of FIG. 3, the duct of arm 28 is of smaller diameter than that of arm 20 such that most of the length of arm 28 is filled with condensate 42, thereby minimizing revaporization of the condensate. A U-shaped portion 44 of the arm 28 traps the condensate 42 for eventual release to reaction chamber 16. The trapped condensate 42 occluding arm 28 effects the selective valving 40 of FIG. 2. The condensate 42 at the discharge end of U-Trap 44 is preferably confined, as by dam 46, to prevent its unrestrained discharge into chamber 16 and flooding of the catalyst surface 18. In fact, the discharge end of U-trap 44 is preferably sufficiently close to the heat source 12 as to be in some degree of heat transfer relationship therewith such that the reactant A of condensate 42 is readily vaporized from the surface 47 of the condensate pool, thereby serving to supply reactant for the endothermic reaction in chamber 16.

Consideration will now be given to the flow dynamics of the working medium. Reference is made to the segments of system 10 illustrated in FIG. 4 and to the respective graphs of temperature and pressure appearing in FIGS. 5a–5d aligned under FIG. 4. The condensate 42 of reactant A extends from near condenser 50, which is positioned relatively close to the exit end of reaction chamber 24 to chill the gaseous reactant A thereat, converting it to its liquid state and thereby rapidly reducing its partial pressure, to a position in relative proximity with the heat source 12 and reaction chamber 16.

Figure 4:
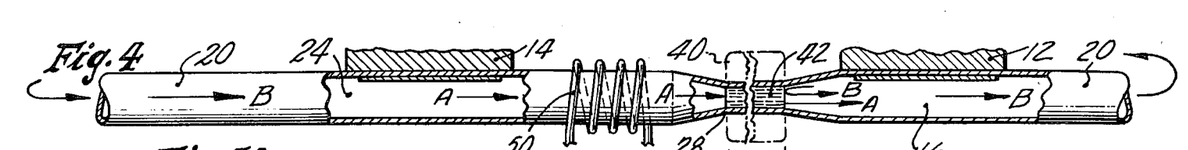
FIG. 4 is an illustration of certain segments of the heat pipe of FIG. 3, shown alinged for graphical purposes.
Figure 5A:
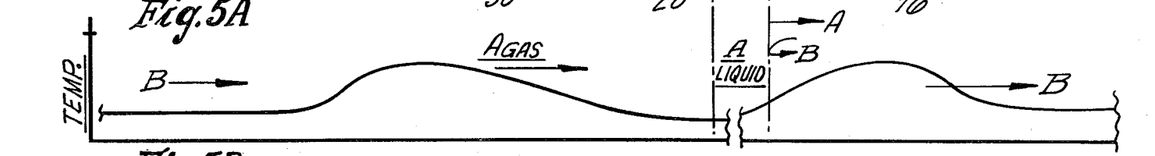
FIG. 5a is a plot of the temperature of the working medium in the heat pipe segments of FIG. 4.

Referring to FIG. 5a, there is illustrated a plot of the relative temperature of the working medium at various locations along the heat pipe system segments illustrated in FIG. 4. Reaction product B, i.e. toluene and hydrogen, may have a temperature near or somewhat above ambient as it approaches heat sink 14. Upon entering reaction chamber 24 and undergoing exothermic reaction, the temperature of the working medium increases to that which will be provided to the heat sink 14. The condenser 50 near the exit from reaction chamber 24 rapidly chills the recombined gaseous reactant A to such extent that it condenses into a liquid. After leaving the cooling region of condenser 50, the working medium, most of which is condensed reactant A, is conducted, as by gravity, to the pool of condensate 42 which is in turn conducted, as by gravity, toward chamber 16. This distance may range from tens or hundreds of feet to many miles and the temperature of the working medium therealong may be near that of the ambient. Because of the proximity of condensate 42 to the heat source 12 at its one end, it begins a gradual increase in temperature with relatively rapid vaporization at its downstream surface. Within the reaction chamber 16, the endothermically reacting working medium undergoes a rapid rise in temperature to a level approximating that of the heat source 12. In the illustrated system, this temperature peak is somewhat greater than that experienced in the reaction chamber 24. Upon exiting from reaction chamber 16, the reaction product B cools or preferably is cooled by a heat recovery system (not shown) to a temperature approximating that of the ambient for the long distance transport to the heat sink 14.

Figure 5B:
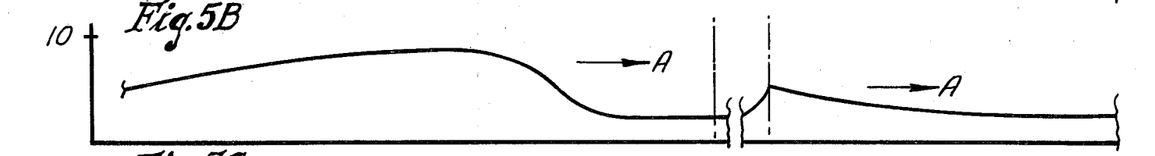
FIG. 5b is a graphical plot of the pressure of the reactant in the heat pipe segments of FIG. 4.

Referring to FIG. 5b, there is graphically illustrated the partial pressure of reactant A at various points along the heat pipe system segments illustrated in FIG. 4. The partial pressure of methylcyclohexane is greatest within reaction chamber 24 wherein reaction product B is converted into gaseous reactant A. Looking leftward in FIG. 5b, a very gradual decline in the partial pressure of reactant A will be experienced because of the depletion of A upstream. However, in the downstream direction from reaction chamber 24, the partial pressure of reactant A is seen to drop dramatically as a result of the condensation effected by condenser 50, such that flow is induced in the desired direction. This partial pressure of reactant A remains relatively low so long as the reactant is in its condensed state, and is seen to undergo a gradual rise as it approaches the heat source 12. However, when reactant A exits from the pool of condensate 42 at its downstream side 47, it is immediately vaporized, is reacted endothermically and is converted to reaction product B in reaction chamber 16. As reactant A is converted to reaction product B, its partial pressure decreases. This decreased partial pressure of reactant A holds through most of the transport path through arm 20 and begins to gradually increase as the region of reaction chamber 24 is approached.

Figure 5C:
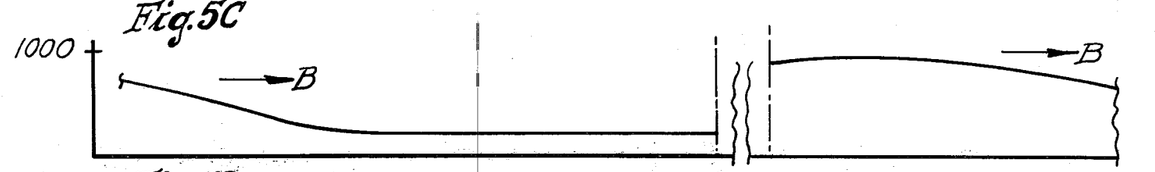
FIG. 5c is a graphical plot of the pressure of the reaction product in the heat pipe segments of FIG. 4.

Referring to FIG. 5c in which the partial pressure of reaction product B is illustrated along the segments of the heat pipe system illustrated in FIG. 4, it will be seen that the partial pressure of the reaction product is usually substantially greater than that of the partial pressure of reactant A, as for instance by a factor of 10 to 1, and has a somewhat inverse relationship as a function of location within the system. Specifically, referring to that location along the graph of FIG. 5c which corresponds with the heat source reaction chamber 16, it is seen that the partial pressure of reaction product B is at a maximum during its formation within that reaction chamber, is reduced slightly upstream toward the stream of condensate as a consequence of the "rightward" flow of reactant A, and slowly declines through arm 20 toward reaction chamber 24. In reaction chamber 24, reaction product B is exothermically reacted to reform the reactant A and thus undergoes a relatively rapid reduction in partial pressure because of its removal thereat from the system. This state of reduced partial pressure for reaction product B extends to the upstream side of the pool of condensate 42. It will be observed that reaction product B is substantially entirely excluded from the region occluded by condensate 42 and thus exhibits no partial pressure thereat.

Figure 5D:
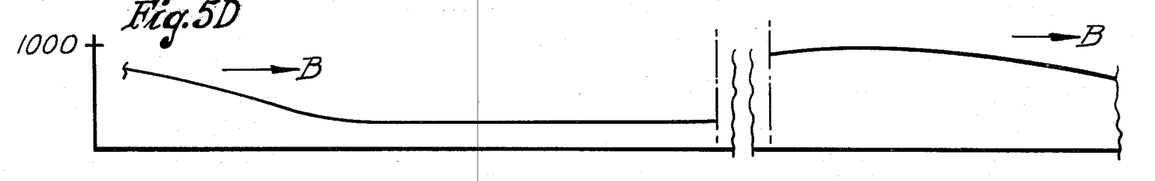
FIG. 5d is a graphical plot of the combined or total pressures of the reactant and reaction product in the heat pipe segments of FIG. 4.

A graph of the combined or total pressures of reactant A and reaction product B is illustrated in FIG. 5d along those segments of the heat pipe system illustrated in FIG. 4. Because the partial pressure of reaction product B is usually so much greater than that of reactant A, the plot of total pressure within the system generally follows that of the partial pressure of reaction product B illustrated in FIG. 5c.

Thus, it is seen that the pressure differential across the pool of condensate 42 resulting from the partial pressure of reaction product B, and thus the total pressure of B plus A is significant, with the greater pressure on the downstream side of the pool in the reaction chamber 16. This pressure differential is manifested by the column of condensate 42 in arm 28 having a level higher than that of surface 47 within the reaction chamber 16. Because the reaction product B cannot flow back through the liquid, i.e. counterclockwise as viewed in FIG. 3, the relatively large pressure existing in reaction chamber 16 serves to drive the working medium clockwise toward the heat sink. Moreover, the largest pressure gradients exhibited by the reactant A are exhibited immediately downstream of reaction chamber 24 in the region of condenser 50 and within reaction chamber 16. These gradients provide the driving force to the reactant A clockwise around the system as viewed in FIG. 3. Thus, it is seen that the reaction product B is driven by a pressure gradient from reaction chamber 16 to reaction chamber 24 via arm 20, and the recombined reactant A is driven or flows from reaction chamber 24 to reaction chamber 16 through arm 28 by means of the pressure gradient effected by condensing the reactant and by gravitational flow of the condensed reactant. The liquid valve 40 effectively prevents the reverse flow of reaction product B.

In view of the foregoing description, it will be seen that a unidirectional flow of the working medium (reactant and reaction product) is established in system 10, which flow is of sufficient capacity to transport substantial quantities of thermal energy a significant distance with minimal losses. The enthalpy removed from the working medium by the condensing action of condenser 50 is quite small compared with the heat of reaction and in any case is recovered as additional cooling at the heat source.

Moreover, the aforedescribed embodiment is inherently self-balancing. For instance, if the temperature at the heat source 12 increases, the rate of vaporization of reactant A from condensate pool surface 47 correspondingly increases, as does its rate of reaction in chamber 16. This acceleration carries through the entire system, resulting in increased thermal energy being delivered to heat sink 14. The volume of condensate pool 42 will remain relatively constant, though increased through-put may be reflected by an increased partial pressure of reaction product B on surface 47 which would alter the relative levels of the ends of condensate pool 42.

Although the foregoing embodiment utilized the condensed reactant A as the sole constituent of liquid pool 42, it would be possible, either alternatively or supplementally, for all or some of that liquid to be a solvent into which the reactant A is dissolved. The reactant A would then be transferred in solution through the arm 28 and U-trap 44 to surface 47 where it would vaporize and react as heretofor described. Such arrangement does not necessarily require the gaseous reactant A leaving chamber 24 to be chilled and condensed, as in the aforedescribed embodiment. Instead, by dissolving the gaseous reactant A in a liquid solvent, the partial pressure of the reactant is greatly reduced and it also enters the liquid form, as desired.

Although the condensed or liquified reactant in return arm 28 preferably occludes that arm for all or most of its length in order to minimize revaporization of the condensate, some voids may exist but the total liquid pressure head must be maintained.

Figure 6:
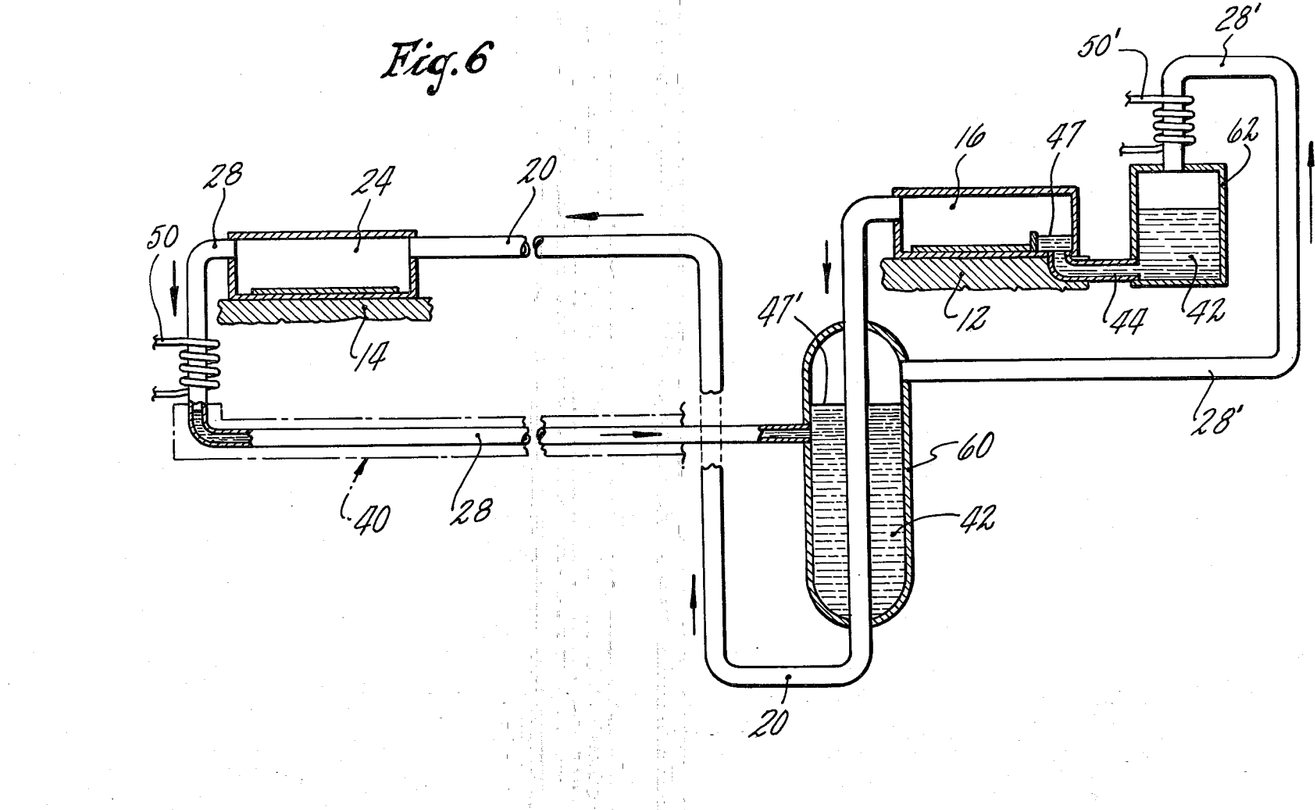
FIG. 6 is a diagrammatical illustration of a self-driven chemical heat pipe in which the heat sink region is lower than the heat source region.

In those situations in which the heat source is located somewhat higher than the heat sink, on the order of tens of feet, it may not be possible to use gravity to aid in the transport of the liquid-form reactant for the entire distance to the heat sink reaction chamber. However, as illustrated in FIG. 6, in which elements similar to like elements in FIG. 3 are similarly numbered, it can be seen that the reactant condensate 42 is readily conducted over the relatively long transport arm 28 to a primary reservoir 60 in which it is collected. The condensate 42 occludes arm 28, preferably over all or most of its length, to provide the selective valve 40. However, because the level of condensate 42 in reservoir 60 is below that of the heat source reaction chamber 16, that condensate is then vaporized, as by heat exchange resulting from passing the heat source end of arm 20 through the condensate in the reservoir. This also has the desirable effect of cooling the reaction product for transport. The reactant is thereby vaporized, forcing it upwardly through relatively short arm 28' to another region of condensation provided by condenser 50' encircling arm 28'. The gaseous reactant is again condensed and is collected as condensate 42 in a secondary reservoir 62 in proximity with reaction chamber 16. A U-trap 44 with reservoir 62 provides a desired secondary valve, and the liquid reactant at surface 47 may be vaporized and endothermically reacted as previously described.

Some control of the rate of thermal transfer to the heat sink may be obtained by the inclusion of one or more selectively variable mechanical control valves (not shown) in the flow path and/or by tapering the wall of dam 46 to vary the area of condensate surface 47, and thereby its rate of vaporization, as a function of the level of the condensate thereat.

Figure 7:
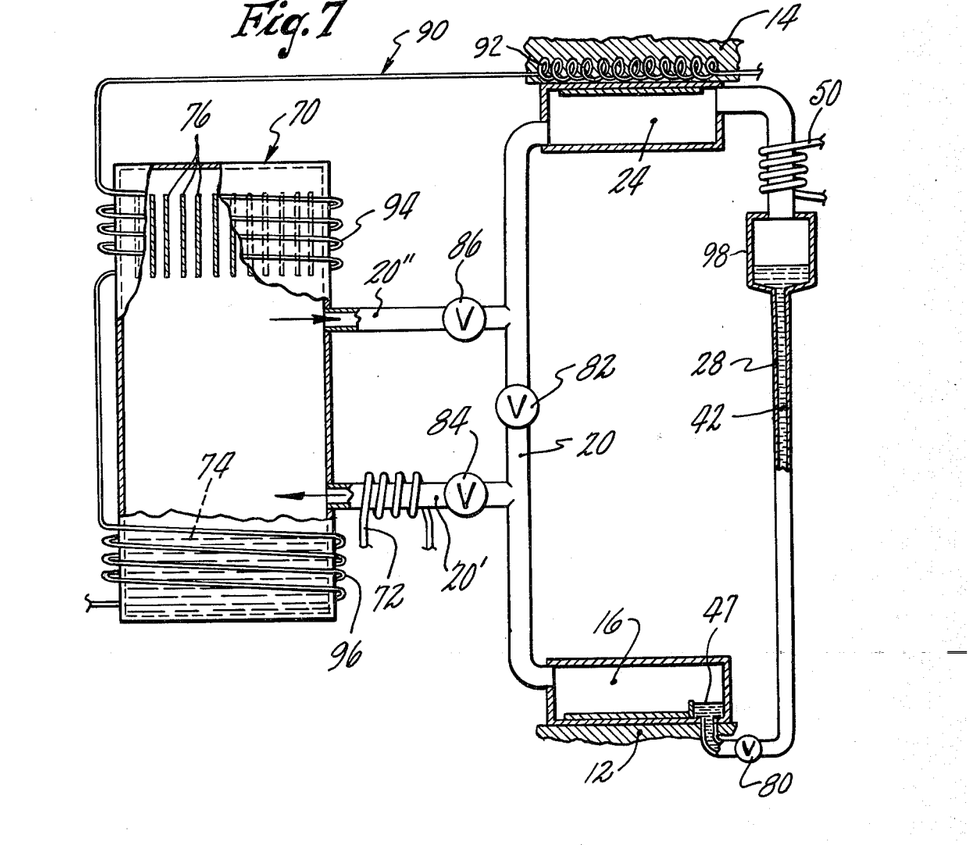
FIG. 7 is a diagrammatical illustration of a self-driven chemical heat pipe including a storage system in accordance with an aspect of the invention.

In accordance with a further aspect of the invention, storage means may be provided for storing the potential thermal energy of the reaction product for an extended period and selectively releasing it to the heat sink region for exothermic reaction when needed. Referring to FIG. 7, there is diagrammatically illustrated a self-driven chemical heat pipe system in part similar to that described with reference to FIG. 3, which similar portions are given the same reference numbers and will not be described in detail. However, in FIG. 7 a storage reservoir 70 is provided for temporarily storing the reaction product for extended periods and for releasing the stored product when it is required for reaction at the heat sink 14. With no demand for heat but with excess high temperature waste energy, the endothermic section of the heat pipe can be operated with the reaction product transferred to storage reservoir 70. In the methylcyclohexane/toluene system, the toluene may be condensed by condenser 72 and stored as a liquid 74 at room temperature and the hydrogen adsorbed on suitable metal surfaces 76. When heat is needed in the low temperature heat sink, an activating heat source can be used to boil off toluene, to desorb hydrogen and to promote the hydrogenation reaction.

More specifically, the primary system includes a primary flow circuit comprised of arms 20 and 28 and the storage system includes a secondary flow circuit comprised of arms 20', 20" and reservoir 70 selectively connectable into and disconnectable from the primary system. Valves 80 and 82 are located in arms 28 and 20 respectively, and valves 84 and 86 are located in arms 20' and 20" respectively. Arm 20' connects to arm 20 intermediate valve 82 and reaction chamber 16, and arm 20" connects to arm 20 intermediate valve 82 and reaction chamber 24. The valving is determined by the temperatures of the source 12 and sink 14, and may be controlled manually or preferably automatically in response to sensed thermal conditions.

Under conventional operating conditions, in which heat source 12 exhibits a high temperature and heat sink 14 exhibits a low temperature, valves 80 and 82 are open and valves 84 and 86 are closed, such that the primary system is operated in the heat transfer manner as hereinbefore described.

However, when the source temperature is high and the sink temperature is also relatively high, heat is available to promote the dehydrogenation reaction but that heat is not required in the sink. Therefore, toluene and hydrogen are stored by having valves 80 and 84 open, and valves 82 and 86 closed. As reaction product transits arm 20' through open valve 84, its toluene is condensed to its liquid form by condenser 72 in heat transfer relation with arm 20'. The liquid toluene 74 is collected and stored in the bottom of reservoir 70 and the gaseous hydrogen may be adsorbed on suitable metal surfaces 76. Alternatively, valve 86 might be left open, the adsorbing surfaces 76 omitted, and the hydrogen gas pressure buildup can be accommodated using most or all of the volume of the entire primary and storage system.

Conversely, when the temperatures of both the sink and the source are low and heat is required by the sink, the stored toluene and hydrogen can be released to the exothermic hydrogenation section by closing valves 80, 82, and 84, opening valve 86 and applying "starting" heat. The "starting" heat is provided by a heater 90 having coils 92 adjacent the catalyst surface of reaction chamber 24, coils 94 adjacent the adsorption plates 76 and coils 96 adjacent the liquid toluene 74. Heater 90 supplies sufficient heat to coils 96 to evaporate toluene, to coils 94 to desorb hydrogen and to coils 92 to initiate the exothermic reaction. Once that exothermic reaction has begun, it will be selfsustaining and no supplemental heat is required thereat any longer; however, such "starting" heat is still required at coils 94 and 96 so long as the stored components are to be discharged from reservoir 70. As previously described, the exothermic reaction in chamber 24 produces gaseous recombined reactant which is condensed by condenser 50 and fills much of arm 28 as condensate 42. However, because the temperature at heat source 12 is too low to sufficiently support the endothermic reaction in chamber 16, it may be desirable to provide arm 28 with sufficient storage capacity for all of the liquified reactant which could result from a complete discharge of reservoir 70. Accordingly, a reservoir 98 is provided in arm 28 closely downstream of condenser 50 for providing such storage capacity and which is preferably of sufficient diameter to retain the additional condensate 42 with relatively little increase in the pressure head in arm 28.

Although this invention has been shown and described with respect to detailed embodiments thereof, it will be understood by those skilled in the art that various changes in form and detail thereof may be made without departing from the spirit and scope of the claimed invention. For instance, the arms 20 and 28 might each comprise plural parallel conduits rather than the singular conduits illustrated; however, their respective functions would not be altered.

We claim:

1. In a chemical heat pipe employing reversible endothermic/exothermic chemical reactions to transfer heat a relatively long distance between a heat source and a heat sink and including a closed circuit flow path in heat transfer relation with a heat source and with a heat sink at respective heat source and heat sink positions along said path, said closed circuit flow path including separate first and second arms each extending between said heat source and heat sink positions, and a chemical reactant being contained within said closed circuit flow path, the method of self-driving said reactant substantially unidirectionally around said closed circuit flow path comprising the steps of:

providing a supply of said reactant in said flow path for reaction at said heat source position;

endothermically reacting at said heat source position said reactant from said supply thereby to create gaseous reaction product at sufficient pressure relative to the pressure at said heat sink position, for establishing flow of said reaction product toward said heat sink position and to enhance transport of said reactant from said supply to said heat source position;

exothermically reacting said reaction product at said heat sink position to reform said reactant in a gaseous state; and converting said reformed reactant to a liquid form and passively conducting said liquid-form reactant toward said heat source position such that it fully occludes at least a portion of said second arm and provides said reactant supply, said occlusion of said second arm by said liquid-form reactant thereby substantially preventing liquid revaporization into an otherwise counterflowing gaseous reaction product and permitting sufficient pressure difference between said heat source and said heat sink positions to establish and promote the flow of said gaseous reaction product to said heat sink position through said first arm.

2. The method of claim 1 wherein said reactant supply comprises said reactant in said liquid form, said supply being in relative proximity to said heat source position.

3. The method of claim 2 wherein said reactant comprises methylcyclohexane and said reaction product comprises toluene and hydrogen, said endothermic reaction thereby dehydrogenating said methylcyclohexane and said exothermic reaction thereby hydrogenating said toluene to reform said methylcyclohexane.

4. The method of claim 1, 2 or 3 wherein said reactant is converted to said liquid form by dissolving said gaseous reactant in a liquid solvent therefor.

5. The method of claim 1, 2 or 3 wherein said reactant is converted to said liquid form by condensing said gaseous reactant.

6. The method of claim 1, 2 or 3 wherein said occluding of at least a portion of said second arm of said flow path with liquid-form reactant includes flowing said liquid-form reactant into a U-trap formed in said second arm sufficient to maintain said trap closed.

7. The method of claim 2 or 3 including the step of vaporizing reactant from said supply of liquid-form reactant preparatory to said step of endothermically reacting said reactant.

8. The method of claim 7 wherein both said steps of endothermically reacting said reactant and exothermically reacting said reaction product are conducted in the presence of respective catalysts.

9. The method of claim 2 or 3 wherein said heat sink position is higher than said heat source position, said reformed reactant is converted to said liquid-form reactant in said second arm in relative proximity to said heat sink position, and gravity aids the flow of said liquid-form reactant toward said heat source position.

10. The method of claim 2 or 3 wherein said heat sink position is lower than said heat source position, said reformed reactant is converted to said liquid-form reactant in said second arm in relative proximity to said heat sink position, said liquid-form reactant is conducted to a location lower than and in relative proximity with said heat source position with substantially no resistance from gravity, and including the further steps of vaporizing said liquid-form reactant at said location below said heat source position, conducting said vaporized reactant upwardly at least to the elevation of said heat source position, and again converting said vaporized reactant to said liquid form thereby to provide said supply in relative proximity to said heat source position.

11. The method of claim 1 including the additional steps of selectively terminating delivery of said reaction product to said heat sink position when it is desired to terminate said exothermic reaction thereat and storing said reaction product created by said endothermic reaction at said heat source while said delivery thereof to said heat sink position is terminated.

12. The method of claim 11 including the further step of selectively delivering said reaction product from storage to said heat sink position for exothermic reaction thereat when said exothermic reaction at said heat source position is unable to provide sufficient reaction product for said exothermic reaction.

13. The method of claim 12 wherein said reaction product comprises at least one constituent and said step of storing said reaction product includes the step of condensing at least one constituent of said reaction product to a liquid state for storage.

14. The method of claim 13 wherein said reaction product comprises at least two constituents and said step of storing said reaction product further includes the step of adsorbing at least one of said constituents.

15. The method of claim 14 wherein said step of delivering said reaction product from storage includes the steps of vaporizing said reaction product constituent stored in the liquid state, desorbing said reaction product constituent stored by absorption, and supplying sufficient heat to said heat sink position for establishing said exothermic reaction.

16. A self-driven chemical heat pipe employing reversible endothermic and exothermic chemical reactions to transfer heat a relatively long distance between a heat source and a heat sink, said heat pipe including means defining a closed circuit flow path in heat transfer relation with a heat source and with a heat sink at respective heat source and heat sink positions along said flow path, said flow path including separate first and second arms each extending between said heat source and heat sink positions, chemical reactant contained within said closed circuit flow path means, said reactant being dissociated by endothermic reaction at said heat source position to form gaseous reaction product, said gaseous reaction product being at sufficient pressure at said heat source position relative to the pressure at said heat sink position for establishing flow of said reaction product toward said heat sink position, said reaction product being recombined by exothermic reaction at said heat sink position to reform said reactant in gaseous form, means for converting gaseous reformed reactant in said second arm to a liquid form, and means for passively conducting said liquid-form reactant toward said heat source position such that it fully occludes at least a portion of said second arm, said occlusion of second arm by said liquid-form reactant thereby preventing flow therethrough of said gaseous reaction product and substantially preventing liquid revaporization to an otherwise counterflowing gaseous reaction product and permitting sufficient pressure difference between said heat source and said heat sink positions to establish and promote the unidirectional flow of said gaseous reaction product to said heat sink position through said first arm.

17. The heat pipe of claim 16 wherein said liquid-form reactant exists and flows substantially only in said second arm such that the flow of said reactant and said reaction product are unidirectional.

18. The heat pipe of claim 17 wherein said means for converting said gaseous recombined reactant to a liquid form comprises condensing means in heat transfer relationship with said flow path.

19. The heat pipe of claim 18 wherein said condensing means is in relative proximity with said heat sink position.

20. The heat pipe of claim 17 wherein said means for converting said gaseous recombined reactant to liquid form comprises a liquid solvent for said reactant, said solvent being in said flow path second arm and said reactant being dissolved in said liquid solvent and being transferred in solution therethrough to relative proximity with said heat source position.

21. The heat pipe of claim 16 wherein said flow path second arm includes a U-trap in relative proximity with said heat source position, said U-trap being filled with said liquid-form reactant.

22. The heat pipe of claim 16 wherein said means for converting said gaseous recombined reactant to liquid form is in relative proximity with said heat sink position, said liquid-form reactant occludes said second arm for most of its length, and said second arm is oriented to minimize the opposition by gravity to said flow of said liquid-form reactant towards said heat source position.

23. The heat pipe of claim 22 wherein said heat sink position is higher than said heat source position and gravity aids said flow of liquid-form reactant.

24. The heat pipe of claim 22 wherein said heat source position is higher than said heat sink position by a relatively small distance, said second arm conducts said liquid-form reactant to an intermediate position lower than said heat source position, and including heating means for vaporizing said liquid-form reactant at said intermediate position, said vaporized reactant being conducted upwardly from said intermediate position to a secondary converting position at least as high as said heat source position, and secondary converting means for reconverting said vaporized reactant to liquid form for passive transport into proximity with said heat source position.

25. The heat pipe of claim 16 wherein said flow path second arm is in sufficient proximity with said heat source at its end proximate said heat source position that said liquid-form reactant is vaporized preparatory to and for said endothermic reaction.

26. The heat pipe of claim 16 wherein said reactant comprises methylcyclohexane and said reaction product comprises toluene and hydrogen.

27. The heat pipe of claim 26 including catalyst means at said respective heat source and heat sink positions for promoting said respective endothermic and exothermic reactions.

28. The heat pipe of claim 16 additionally including means for releasably storing said reaction product, and secondary flow path means communicating with said storage means and being selectively connectable to and disconnectable from said flow path means first arm for selectively storing said reaction product from and returning said reaction product to said flow path means first arm.

29. The heat pipe of claim 28 wherein said reaction product comprises at least two constituents, and including means for condensing at least one of said constituents to a liquid form for storage in said storage means, means in said storage means for adsorbing at least one of said constituents, and selectively operative heating means for vaporizing said liquid constituent and for desorbing said adsorbed constituent preparatory to their said return to said flow path means first arm.

* * * * *